United States Patent [19]
Juhasz et al.

[11] Patent Number: 5,993,438
[45] Date of Patent: Nov. 30, 1999

[54] INTRASTROMAL PHOTOREFRACTIVE KERATECTOMY

[75] Inventors: Tibor Juhasz, Irvine, Calif.; Josef F. Bille, Heidelberg, Germany

[73] Assignee: Escalon Medical Corporation, Skillman, N.J.

[21] Appl. No.: 08/916,082

[22] Filed: Aug. 21, 1997

Related U.S. Application Data

[63] Continuation-in-part of application No. 08/516,581, Aug. 17, 1995, which is a continuation-in-part of application No. 08/151,726, Nov. 12, 1993, abandoned.

[51] Int. Cl.$^6$ .................................................... A61N 5/02
[52] U.S. Cl. ..................................... 606/5; 606/3; 606/10
[58] Field of Search .................................. 606/3–6, 10–19

[56] References Cited

U.S. PATENT DOCUMENTS

| | | |
|---|---|---|
| 3,769,963 | 11/1973 | Goldman et al. . |
| 4,309,998 | 1/1982 | Aron nee Rosa et al. . |
| 4,391,275 | 7/1983 | Frankhauser et al. . |
| 4,538,608 | 9/1985 | L'Esperance, Jr. . |
| 4,580,559 | 4/1986 | L'Esperance, Jr. . |
| 4,601,288 | 7/1986 | Myers . |
| 4,633,866 | 1/1987 | Peyman et al. . |
| 4,653,495 | 3/1987 | Nanaumi . |
| 4,665,913 | 5/1987 | L'Esperance, Jr. . |
| 4,669,466 | 6/1987 | L'Esperance, Jr. . |
| 4,718,418 | 1/1988 | L'Esperance ............................. 606/5 |
| 4,732,148 | 3/1988 | L'Esperance, Jr. . |
| 4,770,172 | 9/1988 | L'Esperance, Jr. . |
| 4,773,414 | 9/1988 | L'Esperance, Jr. . |
| 4,903,695 | 2/1990 | Warner et al. . |
| 4,907,586 | 3/1990 | Belle et al. ............................... 606/5 |
| 4,941,093 | 7/1990 | Marshall et al. . |
| 4,976,709 | 12/1990 | Sand . |
| 4,988,348 | 1/1991 | Bille . |

FOREIGN PATENT DOCUMENTS

| | | |
|---|---|---|
| 0 484 005 | 5/1992 | European Pat. Off. . |
| WO 89/06519 | 7/1989 | WIPO . |
| WO 94/09849 | 5/1994 | WIPO . |

OTHER PUBLICATIONS

L'Esperance, Jr., *Ophthalmic Lasers Photocoagulation, Photoradiation, and Surgery*, pp. 529–538, 1983, The C.V. Mosby Company.

Krauss et al., *Contemporary Technology*, pp. 37–52, Survey of Ophthalmology, vol. 31, No. 1, Jul–Aug., 1986.

John Marshall et al., *Photoablative reprofiling of the cornea using an excimer laser: Photorefractive keratectomy*, pp. 21–45.

*Primary Examiner*—David M. Shay
*Attorney, Agent, or Firm*—Nydegger & Associates

[57] ABSTRACT

A method for performing intrastromal photorefractive keratectomy in the cornea of an eye, using a pulsed, laser beam to photodisrupt a portion of the cornea, includes the initial step of focusing the beam to a focal spot at a selected starting point in the stroma. The starting point is located at a predetermined distance behind the epithelium of the cornea. While focused on the starting point, the laser beam is pulsed to disrupt a volume of the stroma which is approximately equal to the volume of the focal point. Subsequently, the beam is focused in a patterned sequence to focal spots at other discrete points in the stroma. At each point the stroma is photodisrupted. With this progressive pattern of photodisruption, each spot is placed substantially contiguous with adjacent a volume of previously disrupted tissue. The resultant photodisrupted tissue creates a layer which is substantially centro-symmetrical around the optical axis. A plurality of layers can be removed to create a cavity in the stroma. When the cavity collapses, the corneal curvature is changed as desired.

23 Claims, 2 Drawing Sheets

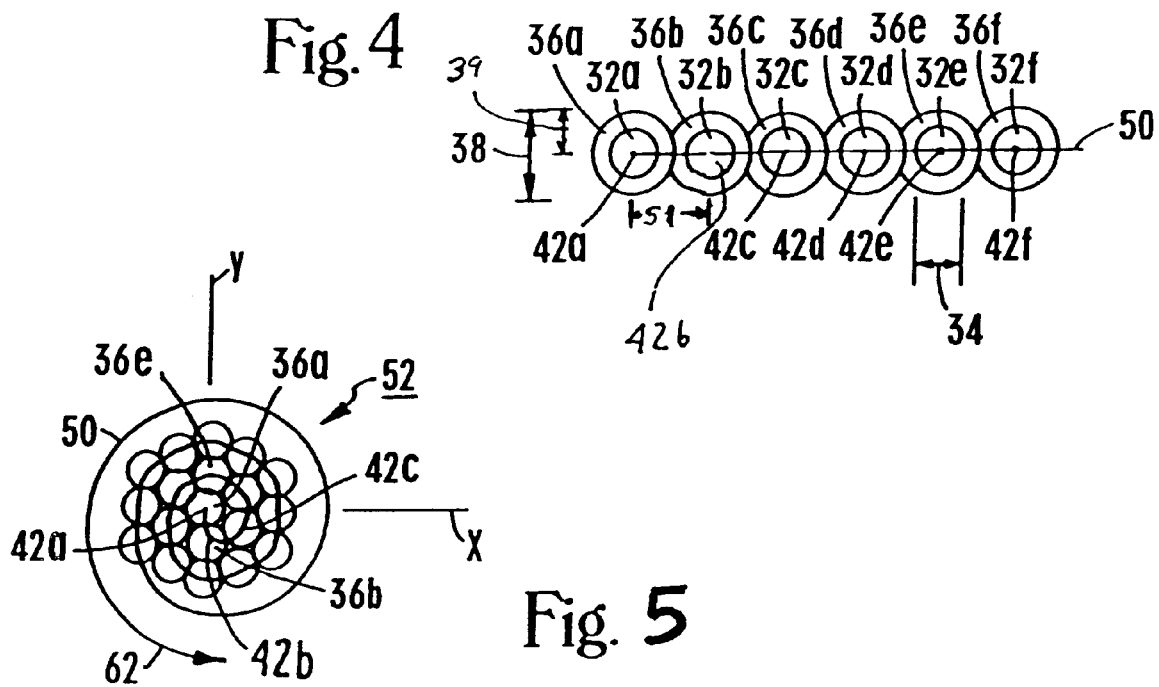

INTRASTROMAL PHOTOREFRACTIVE KERATECTOMY

This Application is a continuation-in-part of co-pending U.S. patent application Ser. No. 08/516,581 filed Aug. 17, 1995, for Intrastromal Photorefractive Keratectomy, which was a continuation-in-part of U.S. patent application Ser. No. 08/151,726 filed Nov. 12, 1993, which is now abandoned. The contents of U.S. patent application Ser. Nos. 08/516,581 and 08/151,726 are incorporated herein by reference.

FIELD OF THE INVENTION

The present invention pertains to a method for using lasers to accomplish ophthalmic surgery. More particularly, the present invention pertains to methods for reshaping the cornea of the eye to improve a patient's vision. The present invention is particularly, but not exclusively, useful as a method for intrastromal photorefractive keratectomy (hereinafter "ISPRK").

BACKGROUND OF THE INVENTION

It is known that the cornea of an eye can, in certain instances, be surgically reshaped to correct and improve vision. Where the condition being corrected is myopia or near-sightedness, the cornea is relatively flattened, whereas if hyperopia is being corrected, the cornea is relatively steepened.

In either case, as more fully set forth below, there are several different types of ophthalmic surgical procedures which can be employed for this purpose. Although the types of procedures may vary, the ultimate object in correcting myopia, for example, is the same. Namely, the object is to cause different types of tissues in the cornea. These include portions of the epithelium, Bowman's membrane, and the stroma.

The present invention recognizes that it is preferable to leave the epithelium and Bowman's membrane intact and to limit the tissue removal to only the stroma. Removal of tissue from the stroma results in the creation of a specially shaped cavity in the stroma layer of the cornea. When the cornea deforms in the intended manner, the desired flattening of the cornea results.

Further, the present invention recognizes that internal tissue "photodisruption," can be effectively accomplished using a pulsed laser energy if the irradiance of the beam, its focal spot size, and the proper layering of photodisruption sites are effectively controlled.

Accordingly, it is an object of the present invention to provide an improved method for performing intrastromal photodisruption on the cornea of an eye. Still another object of the present invention is to provide a method for intrastromal photodisruption which removes stromal tissue in a predetermined pattern to attain the desired flattening of the cornea. Yet another object of the present invention is to provide a method for intrastromal photodisruption which is relatively easy to perform and which is comparatively cost effective.

SUMMARY

In accordance with the present invention, a method for performing photodisruption and removal of tissue in a stroma in a cornea of an eye uses a pulsed laser beam which is sequentially focused to individual spots at a plurality of points in the stroma. Each focus spot has a finite volume, rather than being a single point. Further, each spot has a central point at approximately the center of the finite volume. Photodisruption of stromal tissue occurs at each spot where the beam is focused and the volume of stromal tissue disrupted at each spot is approximately equal to the volume of the spot. The photodisrupted tissue is absorbed into or removed from the cornea through well known means. The spots are arranged in successive spiral patterns to photodisrupt and remove a plurality of layers of stromal tissue, with the diameters of the layers being properly sized to result in the desired diopter correction.

The physical characteristics of the laser beam, as well as the manner of focusing the laser beam, are important to the proper performance of the method of the present invention. As indicated above, these considerations are interrelated.

First, insofar as the characteristics of the laser beam are concerned, several factors are important. The laser beam should have a wavelength that allows the light to pass through the cornea without absorption by the corneal tissue. Accordingly, the light in the laser beam will not be absorbed as the beam transits through the cornea until it reaches the focal spot. Generally, the wavelength should be in the range of three-tenths of a micrometer (0.3 $\mu$m) to three micrometers (3.0 $\mu$m), with a wavelength of one thousand fifty-three nanometers (1,053 nm) being preferred. The irradiance of the beam for accomplishment of photodisruption of stromal tissue at the focal spot should be greater than the threshold for optical breakdown of the tissue. The irradiance which will cause optical breakdown of stromal tissue is approximately two hundred gigawatts per square centimeter (200 GW/cm$^2$) at a pulse duration of approximately fifty pico seconds. Preferably, the irradiance should not be more than ten (10) times greater than the threshold for optical breakdown. Further, the pulse repetition frequency of the pulsed laser beam is preferably in the range of approximately one Hertz to ten Hertz (1 kHz–10 kHz).

Second, insofar as the focusing of the laser beam is concerned, spot size, spot configuration, and spot pattern are all important. The spot size of the focused laser beam should be small enough to achieve optical breakdown of stromal tissue at the focal spot. Typically, this requires the spot size to be approximately ten micrometers (10 $\mu$m) in diameter. Additionally, it is preferable that the spot configuration be as close to spherical as possible. To achieve this configuration for the spot it is necessary that the laser beam be focused from a relatively wide cone angle. For the present invention, the cone angle will preferably be in the range of fifteen degrees to forty-five degrees (15°–45°). Finally, the spots must be arranged in a pattern that is optimal for creating a cavity of the desired shape. The subsequent deformation of the cavity results in the ultimate reshaping of the cornea in the desired fashion to achieve a desired refractive effect.

To perform intrastromal photodisruption in accordance with the method of the present invention the laser beam is focused at a first selected spot at a starting point in the stroma. For myopic corrections, the starting point is preferably on the optical axis of the eye at a location behind the epithelium. The laser beam is then activated and the stromal tissue at the first spot is photodisrupted. Importantly, because spot size and configuration and the irradiance level of the laser beam are closely controlled for the present invention, the volume of stromal tissue which is photodisrupted and removed at the focal spot is carefully controlled. Preferably, this volume is about the same as the volume occupied by the focal spot, and has a volume diameter of between about ten micrometers (10 $\mu$m) to twenty-five micrometers (25 $\mu$m) diameter spherical volume.

Next, the laser beam is focused at a second selected spot in the stroma, proximate the first focal spot. It should be noted, however, that during photodisruption of the stromal tissue, a cavitation bubble results which has a bubble radius which is approximately equal to or larger than the spot diameter of the focal spot. Therefore, the second focal spot is selected at a point in the stroma which is substantially adjacent to the cavitation bubble resulting from the first focal spot. Again, the laser beam is activated and stromal tissue at the second spot is photodisrupted to add to the volume of stromal tissue which had previously been photodisrupted. Because of the placement of the second spot relative to the cavitation bubble from the first spot, there preferably is some overlap between the cavitation bubbles at the two (2) spots. This process is continued, proceeding from point to point along a spiral through the stroma, until a ten micrometer (10 $\mu$m) thick layer of stromal tissue has been photodisrupted and removed. The layer of photodisrupted tissue is substantially symmetrical to the optical axis.

For effective vision correction of the eye using intrastromal photorefractive keratectomy techniques, it is preferable that tissue photodisruption be accomplished at a plurality of adjacent points in a patterned sequence to create a plurality of layers of tissue removal. The object is to create a dome shaped cavity within the stromal tissue. The dome shaped cavity subsequently collapses, reshaping the corneal surface.

The present invention contemplates that the adjacent focal spots in a given cavity layer of the stroma can all be located in a plane which is perpendicular to the optical axis of the eye. Further, in this embodiment, the pattern of spots in each layer can be positioned in a spiral pattern which is substantially centro-symmetric to the optical axis of the eye. The result is a plurality of substantially flat layers of photodisrupted stromal tissue, each layer being substantially perpendicular and substantially symmetric to the optical axis.

Alternately, the present invention provides that the adjacent focal spots in a given cavity layer of the stroma can be positioned so that each cavity layer has a substantially curved cross-section. The result is a plurality of curved cavity layers of photodisrupted stromal tissue, each cavity layer being substantially symmetric to the optical axis.

Importantly, to obtain effective vision correction, the consecutive focal spots must be properly spaced apart. For example, if the focal spots are too close together, too much heat may develop in the eye. Alternately, if the consecutive focal spots are too far apart, the vision may not be properly corrected. As provided by the present invention, a spot distance between consecutive focal spots is preferably between approximately one (1) to two (2) times the bubble radius and more preferably between approximately one and one-half (1.5) to one and nine-tenths (1.9) times the bubble radius.

In accordance with the present invention, a plurality of superposed photodisrupted layers can be created by first photodisrupting the layer which is to be farthest from the epithelium, followed by successive photodisruption of additional layers in an anterior progression. Each successive layer in the anterior progression has a smaller outer diameter than the previous layer. The amount by which each layer is smaller than the previous one is determined by a particular geometric model which has been devised to result in the creation of the desired dome shaped cavity. Regardless of the number of layers created, it is important that every layer be at a safe distance form the epithelium, e.g., no closer than approximately thirty micrometers (30 $\mu$m).

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 4 is a schematic representation of the relative positioning of adjacent laser beam spots and the resultant overlapping disruption of stromal tissue which occurs during implementation of the method of the present invention; and FIG. 5 is a plan view schematic representation of a predetermined spiral pattern of focal spots and the resultant layer in which stromal tissue is photodisrupted by implementation of the method of the present invention.

DESCRIPTION

Figure 1:
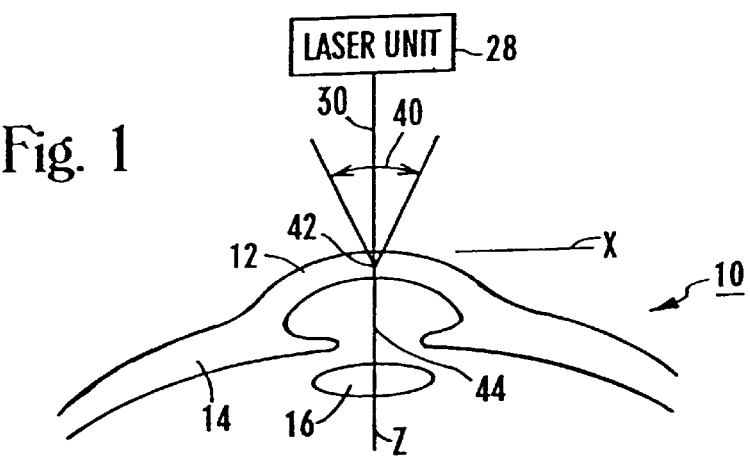
FIG. 1 is a cross-sectional view of the cornea of an eye shown in relationship to a schematically depicted laser unit.

Referring initially to FIG. 1, a cross-section of part of an eye is shown and generally designated 10. For reference purposes, the portion of eye 10 which is shown includes the cornea 12, the sclera 14, and the lens 16. Further, in accordance with standard orthogonal ocular referencing coordinates, the z-axis or z direction is generally oriented on the optical axis of the eye 10. Consequently, the x and y directions establish a plane which is generally perpendicular to the optical axis.

Figure 2:
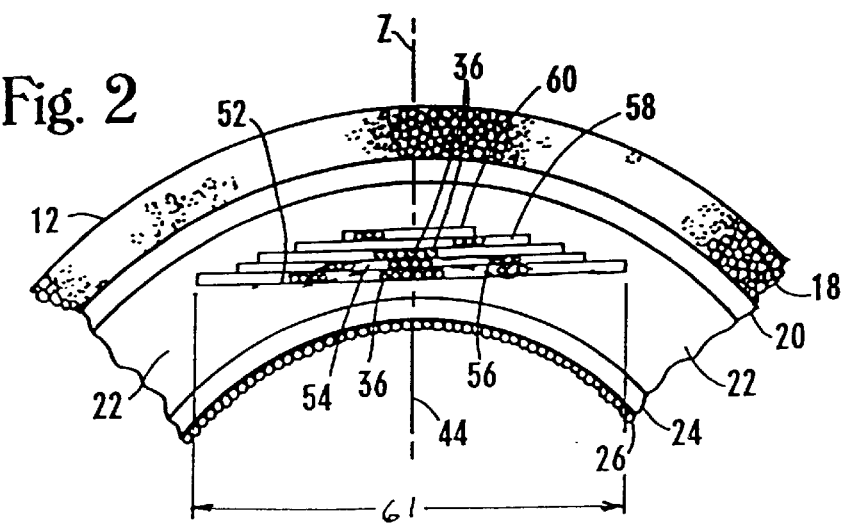
FIG. 2 is a cross-sectional view of the cornea of an eye showing one embodiment of the cavity layers in the eye.
Figure 3:
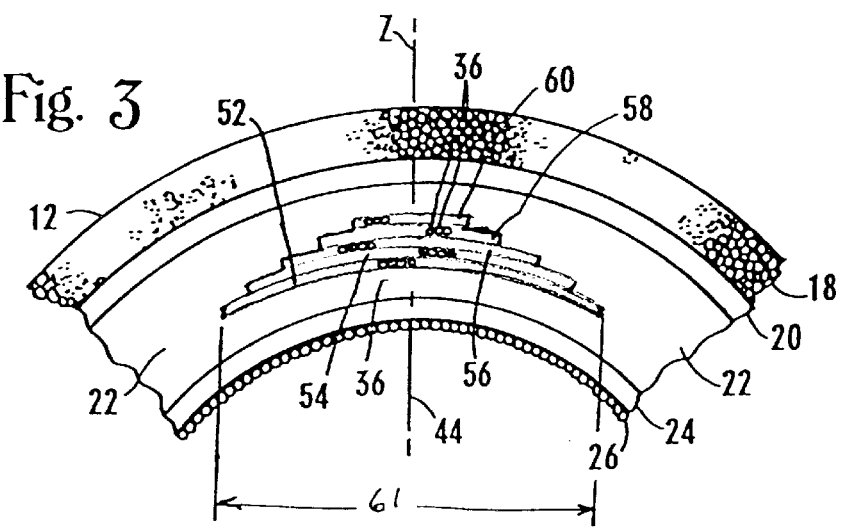
FIG. 3 is a cross-sectional view of the cornea of an eye showing a second embodiment of the cavity layers in the eye.

As can best seen in FIGS. 2 and 3, the anatomy of the cornea 12 of an eye 10 includes five (5) different identifiable tissues. The epithelium 18 is the outermost tissue on the exterior of the cornea 12. Behind the epithelium 18, and ordered in a posterior direction along the z-axis, are Bowman's membrane 20, the stroma 22, Descemet's membrane 24, and the endothelium 26. Of these various tissues, the region of most interest to the present invention is the stroma 22.

Returning for the moment to FIG. 1, it will be seen that the method of the present invention incorporates a laser unit 28 which must be capable of generating a pulsed laser beam 30 having certain characteristics. Importantly, the pulsed laser beam 30 should be monochromatic light having a wavelength (X) which will pass through all tissues of the cornea 12 without interacting with those tissues. Preferably, wavelength ($\lambda$) of laser beam 30 will be in the range of from three tenths of a micrometer to three micrometers ($\lambda$=0.3 $\mu$m to 3.0 $\mu$m). Also, the pulse repetition rate of laser beam 30 should be approximately in the range of from one hundred Hertz to one hundred thousand Hertz (0.1 kHz to 100 kHz).

An additional factor of great importance to the present invention is that the irradiance of laser beam 30 must be circumscribed and well defined. The main concern here is that the irradiance of beam 30 will, in large part, determine the photodisruptive capability of pulsed laser beam 30 on tissue of the stroma 22.

Irradiance, or radiant flux density, is a measure of the radiant power per unit area that flows across a surface. As indicated by the following expression, the irradiance of laser beam 30 is a function of several variables. Specifically:

$$\text{Irradiance} = \frac{(\text{pulse energy})}{(\text{pulse duration})(\text{spot size})}$$

From the above expression for irradiance it can be appreciated that, for a constant level of irradiance, the irradiance is proportional to the amount of energy in each pulse of beam 30. On the other hand, irradiance is inversely proportional to pulse duration and spot size. The significance of this functional relationship stems from the fact that the irradiance of pulsed laser 30 should be approximately equal to the optical breakdown threshold for stromal tissue 22. This threshold is known to be about two hundred gigawatts per square centimeter (200 GW/cm$^2$) for a pulse duration of approximately fifty pico seconds (50 psec). Insofar as each factor's contribution to irradiance is concerned, it is important to recognize that no one (1) factor can be considered individually. Instead, the pulse energy, pulse duration, and focal spot size of laser beam 30 are interrelated and each characteristic is variable.

For purposes of the present invention, the pulse duration of pulses in laser beam 30 is preferably in the range of from one hundred femtoseconds (100 fs) to ten nanoseconds (10 ns). As for the spot size to which each pulse is focused, the determinative consideration is that the spot size should be small enough to achieve optical breakdown in a volume of stromal tissue 22 which is approximately equal to the volume of the focal spot. This relationship is perhaps best seen in FIG. 4.

In FIG. 4, a succession of focal spots 32a–32f are shown. All focal spots 32a–32f are substantially spherical or slightly ellipsoidal and have substantially the same volume. As such, they can each be characterized as having a spot diameter 34. Focal spots 32a–32f are shown arranged in a straight line 50 for the sake of simplicity of the drawing, but as will be explained, for the present invention, it is preferable for the focal spots 32a–32f to be arranged on a spiral path. FIG. 4 also shows the general relationship between each focal spot 32a–32f and the associated cavitation bubble 36a–36f which results when laser unit 28 is activated to irradiate a focal spot 32a–32f. The cavitation bubble 36a–36f, like the associated focal spot 32a–32f, will be generally spherical and can be characterized by a bubble diameter 38 and a bubble radius 39.

As indicated above, it is preferable that diameter 38 of each of the cavitation bubbles 36a–36f be the same as the diameter 34 of the corresponding focal spot 32a–32f. This, however, cannot always be achieved. In any event, it is important that the volume of cavitation bubble 36a–36f not be significantly larger than the volume of the focal spot 32a–32f. For the present invention, it is important that the diameter 34 of focal spots 32a–32f be less than about one hundred micrometers (1 00 μm) and preferably about ten micrometers (10 μm). It is preferable that the diameter 38 of cavitation bubbles 36a–36f be no more than about twice the diameter 34 of focal spots 32a–32f.

As indicated above, the focal spots 32a–32f are substantially spherical. To configure focal spots 32a–32f as close as possible to a sphere, rather than as an elongated ellipsoid, it is necessary for laser beam 30 to be focused through a rather wide cone angle 40 (See FIG. 1). For purposes of the method of the present invention, cone angle 40 should be in the range of from fifteen degrees to forty-five degrees (15°–45°). Presently, the best results are known to be achieved with a cone angle of about thirty-six degrees (36°).

For the practice of the method of the present invention, it is first necessary for the physician to somehow stabilize the eye 10. A suitable device for stabilizing the eye 10 is provided for in U.S. Pat. No. 5,336,215, issued to Hsueh et al. and entitled "Eye Stabilizing Mechanism for Use in Ophthalmic Laser Surgery." After the eye 10 has been stabilized, laser beam 30 is focused on a focal spot 32a at a first selected focal spot central point 42a in the stroma 22. Specifically, for many procedures, the first focal spot central point 42a is located generally on the z-axis 44 behind the Bowman's membrane 20. As used here, "behind" means in a posterior direction or inwardly from the Bowman's membrane. Once laser beam 30 is so focused, the laser unit 28 is activated to irradiate the focal spot 32a at first focal spot central point 42a. The result is that a cavitation bubble 36a is formed in stromal tissue 22, and a corresponding volume of stromal tissue is disrupted and removed from the stroma 22.

The physical consequences of photodisruption of stromal tissue 22 at the first focal point 42a and at other focal points 42b–42f is, of course, removed. Additionally, however, by-products such as carbon dioxide ($CO_2$), carbon monoxide (CO), nitrogen ($N_2$) and water ($H_2O$) are formed. As stated above, these by-products create a cavitation bubble 36a–36f in the tissue of stroma 22. The volume of tissue removed is approximately the same as the volume of the cavitation bubble 36a–36f.

As indicated in FIG. 4, once the cavitation bubble 36a has been created, the laser beam 30 is repositioned for refocusing at another point 42b. In FIG. 4, it is shown that the second focal spot central point 42b is substantially adjacent to the first focal spot central point 42a and that both the second focal spot central point 42b and first focal spot central point 42a lie on a path 50. Importantly, the distance along path 50 between first focal spot central point 42a and second focal spot central point 42b is selected so that the adjacent volumes of disrupted tissue in cavitation bubbles 36a, 36b will preferably overlap. In effect, the size of the cavitation bubbles 36a–36f of disrupted tissue volume will determine the separation distance between selected focal spot central points 42a–42f along the path 50.

As implied here, subsequent focal points 42c et seq. will also lie on the predetermined path 50 and the disrupted tissue volume at any respective focal spot central point 42 will preferably overlap with the volume of tissue disrupted at the previous focal point in stroma 22. Consequently, a separation spot distance 51 between focal spot central points 42 on path 50 must be established so that tissue removal along the path 50 will be substantially continuous. As provided herein, the spot distance 51 between consecutive focal spots is preferably between approximately one (1) to two (2) times the bubble radius 39 and more preferably between approximately one and one-half (1.5) to one and nine-tenths (1.9) times the bubble radius 39.

FIG. 5 shows a plan view of a photodisrupted layer 52 as seen looking toward the eye 10 along z-axis 44. Also, FIG. 5 shows that the first focal spot central point 42a and the sequence of subsequent points 42b–42f all lie along the path 50. Further, FIG. 5 shows that the path 50 can be set as a pattern 62 and, as shown in FIG. 5, this pattern 62 can be a spiral pattern. It is to be appreciated that the spiral pattern 62 can be extended as far as is desired and necessary to create the layer 52 of disrupted tissue volumes 36. Further, it is to be appreciated that layer 52 may be curved to generally conform to the shape of the cornea's external surface. It is also to be appreciated that the final pattern 62 will be approximately centro-symmetric with respect to the optical axis (z-axis 44) of the eye 10.

Referring back to FIG. 2, in one embodiment of the present invention, it will be seen that a plurality of disrupted tissue volumes 36 can be juxtaposed to establish a continuous layer 52 of disrupted stromal tissue. Only a few of the disrupted tissue volumes 36 are shown in layer 52, for the sake of clarity of the drawing, but it should be understood that the entire layer 52 is disrupted as discussed above. As shown in FIG. 2, a plurality of layers can be created in stroma 22 by the method of the present invention. FIG. 2 shows a layer 54 which is located in front of the layer 52 and a layer 56 which is located in front of the layer 54. Layers 58 and 60 are also shown, with layer 60 being the most anterior and smallest in diameter. As with layer 52, layers 54, 56, 58, and 60 are entirely created by a plurality of disrupted tissue volumes 36. At least approximately ten (10) of these layers can be so created, if desired.

Whenever a plurality of layers is to be created, it is preferable that the most posterior layer be created first and that each successive layer be created more anteriorly than any previously created layer. For example, to create layers 52, 54, 56, 58, and 60, it is necessary to start first with the creation of the layer 52. Then, in order, layers 54, 56, 58, and 60 can be created.

As shown in FIG. 2, each cavity layer 52, 54, 56, 58, and 60 is substantially flat, substantially planer, and substantially perpendicular to the optical axis 44 of the eye 10. Further, each cavity layer has a cavity outer diameter 61.

There are limitations as to how close any layer can be to the epithelium, 18 in order to avoid unwanted photodisruption of Bowman's membrane 20 and the epithelium 18. Accordingly, no disrupted tissue volume 36 in any layer should be closer to the epithelium 18 than approximately thirty microns (30 $\mu$m). Therefore, because it is anticipated that each layer will effectively encompass approximately a ten microns (10 $\mu$m) to fifteen microns (15 $\mu$m) thickness of tissue, it is necessary that the first layer 52 be created at an appropriate location so that neither layer 52 nor any subsequent layer should eventually be located closer to the epithelium 18 than thirty microns (30 $\mu$m).

For a required myopic correction, it is desired to decrease the amount of corneal curvature by a given number of diopters (D), by increasing the corneal radius of curvature. Such a change in corneal curvature is accomplished by removing certain layers of the stromal tissue to create a dome shaped cavity entirely within the stromal layer 22. This cavity will then collapse, resulting in a flattening of the corneal anterior surface. This flattening will achieve the desired corneal curvature change. The desired corneal curvature change D in diopters can be computed according to the following equation:

$$D = \frac{2(n-1)\left(\rho_0\left[1-\left(1-\left(\frac{d_0}{2\rho_0}\right)^2\right)^{1/2}\right]-Nt\right)}{\left(\rho_0\left[1-\left(1-\left(\frac{d_0}{2\rho_0}\right)^2\right)^{1/2}\right]-Nt\right)^2 + \frac{d_0^2}{4}} - \left(\frac{n-1}{\rho_0}\right)$$

where N is the selected number of intrastromal layers to be used to achieve the curvature change. The thickness of each layer, such as ten microns (10 82 m) in the example given, is represented by t. The index of refraction of the cornea is represented by n. The corneal radius of curvature is $\rho$, with $\rho_0$ being the preoperative radius. The selected cavity outer diameter of the intrastromal cavity to be created, keeping in mind the minimum required separation from the epithelium 18, is given by $d_0$. This selected outer diameter becomes the outer diameter 61 of the first layer to be created. More effect is produced with smaller cavity outer diameters and with more layers. The sensitivity to cavity diameter decreases sharply over a cavity diameter of approximately five millimeters (5 mm).

For myopic correction, the outer diameter 61 of each layer 52, 54, 56, 58, and 60 is smaller than the outer diameter 61 of the layer previously created, to create a dome shaped cavity with its base oriented posteriorly, and its crown oriented anteriorly. A geometric analysis of the change in corneal curvature upon collapse of an intrastromal cavity has revealed the optimum shape of the cavity. The appropriate diameter for each layer, $d_i$, to achieve a desired correction of the anterior corneal curvature, is calculated according to the following equation:

$$d_i = 2\rho_0\left(1 - \left[\frac{(\rho_0 D + n - 1)(\rho_0 - t(i-1/2))^2 + (\rho_0 - Nt)[(\rho_0 D + n - 1)(\rho_0 - Nt) - 2(n-1)\rho_0]}{2[\rho_0^2 D - Nt(\rho_0 D + n - 1)](\rho_0 - t(i-1/2))}\right]^2\right)^{1/2}$$

where i designates the layer for which the diameter is being calculated and i=1,2,3, . . . , N.

Table 1 lists the layer diameters, in millimeters, which would result from the selection of an outer treatment zone diameter, or cavity diameter, of six millimeters (6.0 mm), where N, the number of intrastromal layers, varies from two to ten (2–10). The first layer has the same diameter as the treatment zone. The preoperative corneal radius of curvature is assumed to be eight millimeters (8.0 mm) and each layer is assumed to have a thickness of ten micrometers (10 $\mu$m). The expected resultant change in corneal radius of curvature is listed at the bottom of each column.

TABLE 1

| Layer | N = 2 | N = 3 | N = 4 | N = 5 | N = 6 | N = 7 | N = 8 | N = 9 | N = 10 |
|---|---|---|---|---|---|---|---|---|---|
| 1 | 6.000 | 6.000 | 6.000 | 6.000 | 6.000 | 6.000 | 6.000 | 6.000 | 6.000 |
| 2 | 3.044 | 4.285 | 4.779 | 5.051 | 5.223 | 5.343 | 5.430 | 5.497 | 5.550 |
| 3 |  | 2.490 | 3.721 | 4.286 | 4.622 | 4.847 | 5.009 | 5.130 | 5.225 |
| 4 |  |  | 2.159 | 3.334 | 3.920 | 4.288 | 4.543 | 4.731 | 4.875 |
| 5 |  |  |  | 1.932 | 3.047 | 3.635 | 4.017 | 4.289 | 4.495 |
| 6 |  |  |  |  | 1.765 | 2.824 | 3.404 | 3.792 | 4.075 |
| 7 |  |  |  |  |  | 1.635 | 2.644 | 3.213 | 3.602 |
| 8 |  |  |  |  |  |  | 1.530 | 2.495 | 3.051 |
| 9 |  |  |  |  |  |  |  | 1.444 | 2.368 |
| 10 |  |  |  |  |  |  |  |  | 1.370 |
|  | −1.50 | 2.26 | −3.02 | −3.78 | −4.54 | −5.31 | −6.08 | −6.85 | −7.62 |

In Other embodiment shown in FIG. 3, a plurality of disrupted tissue volumes 36 are again juxtaposed to establish a continuous layer 52 of disrupted stromal tissue. Again, only a few of the disrupted tissue volumes 36 are shown in layer 52, for the sake of clarity of the drawing, but it should be understood that the entire layer 52 is disrupted as discussed above. Similar to FIG. 2, layer 54 is located in front of the layer 52 and layer 56 is located in front of the layer 54. Layers 58 and 60 are also shown, with layer 60 being the most anterior and smallest in diameter.

In the embodiment shown in FIG. 3, each layer 52, 54, 56, 58, and 60 has a substantially curved cross-section and is substantially symmetrical with the optical axis 44 of the eye. Stated another way, each layer 52, 54, 56, 58, and 60 is shaped somewhat similar to a segment of a sphere. Preferably, each layer has a curve which is substantially similar to the curve of the eye 10.

While the particular method for performing intrastromal photorefractive keratectomy on the cornea of an eye using a pulsed laser beam as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

What is claimed is:

1. A method for modifying the curvature of the cornea of an eye, the eye including a stroma and an optical axis, the cornea including an anterior surface, the method comprising the steps of:

focusing a laser beam through the anterior surface of the cornea to a plurality of focal spots in the stroma;

pulsing the laser beam to modify a plurality of substantially contiguous volumes of stromal tissue at the plurality of focal spots to create a first cavity layer; and repeating the focusing step and the pulsing step to create a plurality of additional cavity layers within the stroma in an anterior progression.

2. A method as recited in claim 1 wherein each focal spot has a central point, and the step of focusing the laser beam includes focusing the laser beam so that the central point of successive focal spots are spaced apart a spot distance which is equal to between approximately one to two times the bubble radius.

3. A method as recited in claim in claim 2, wherein the step of focusing the laser beam includes focusing so that the spot distance is equal to between approximately 1.5 times to 1.9 times the bubble radius.

4. A method for modifying the curvature of the cornea of an eye, the eye including a stroma and an optical axis, the cornea including an anterior surface, the method comprising the steps of:

focusing a laser beam through the anterior surface of the cornea to a plurality of focal spots in the stroma;

pulsing the laser beam to photodisrupt a plurality of substantially contiguous volumes of stromal tissue at the plurality of focal spots to create a first cavity layer within the stroma having a first cavity outer diameter, the first cavity layer being substantially symmetrical to the optical axis; and repeating the focusing step and the pulsing step to create a plurality of additional cavity layers within the stroma in an anterior progression, the plurality of additional cavity layers having progressively smaller cavity outer diameters.

5. A method as recited in claim 4, further comprising the step of selecting the focal spots for each cavity layer so that each cavity layer is substantially flat, substantially circular, and substantially perpendicular to the optical axis.

6. A method as recited in claim 4, further comprising the step of selecting the focal spots for each cavity layer so that each cavity layer has a substantially curved cross-section.

7. A method as recited in claim 4 wherein each focal spot has a central point, and the step of focusing the laser beam includes focusing the laser beam so that the central point of successive focal spots are spaced apart a spot distance which is equal to between approximately one to two times the bubble radius.

8. A method as recited in claim 7, wherein the step of focusing the laser beam includes focusing so that the spot distance is equal to between approximately 1.5 times to 1.9 times the bubble radius.

9. A method as recited in claim 4, further comprising the step of selecting the focal spots for each said cavity layer in a spiral pattern.

10. A method as recited in claim 9, further comprising the step of arranging the spiral pattern to be substantially centro-symmetric relative to the optical axis of the eye.

11. A method for modifying the curvature of a cornea of an eye, the eye including a stroma and an optical axis, the cornea including an anterior surface, the method comprising the steps of:

focusing a laser beam through the anterior surface of the cornea to a plurality of focal spots in the stroma, each focal spot having a central point, wherein the central point of consecutive focal spots are spaced apart approximately a spot distance;

pulsing the laser beam to photodisrupt the stroma at the plurality of focal spots to create a plurality of cavitation bubbles in the stroma, each cavitation bubble having a bubble radius which is substantially the same for all of the cavitation bubbles, the cavitation bubbles forming a first cavity layer within the stroma having a first cavity outer diameter, the first cavity layer being substantially symmetric to the optical axis; and repeating the focusing step and the pulsing step to create a plurality of additional cavity layers within the stroma in an anterior progression, the plurality of additional cavity layers having progressively smaller cavity outer diameters and being substantially symmetric to the optical axis;

wherein, the spot distance is equal to between approximately one to two times the bubble radius.

12. A method as recited in claim 11, wherein the step of focusing the laser beam includes focusing so that the spot distance is equal to between approximately 1.5 times to 1.9 times the bubble radius.

13. A method as recited in claim 11, further comprising the step of calculating each cavity outer diameter of each cavity layer according to the equation:

$$d_i = 2\rho_0 \left(1 - \left[\frac{(\rho_0 D + n - 1)(\rho_0 - t(i - 1/2))^2 + (\rho_0 - Nt)[(\rho_0 D + n - 1)(\rho_0 - Nt) - 2(n-1)\rho_0]}{2[\rho_0^2 D - Nt(\rho_0 D + n - 1)](\rho_0 - t(i - 1/2))}\right]^2\right)^{1/2}.$$

14. A method as recited in claim 11, further comprising the step of selecting the focal spots for each cavity layer in a spiral pattern.

15. A method as recited in claim 14, further comprising the step of arranging the spiral pattern to be substantially centro-symmetric relative to the optical axis of the eye.

16. A method as recited in claim 11, further comprising the step of selecting a laser beam having a wavelength in a range between three tenths of a micron (0.30 μm) and three micrometers (3.0 μm), a pulse frequency in a range between one hundred Hertz (100 kHz) and one hundred thousand Hertz (1,000,000 kHz), and an irradiance which is substantially equal to or exceeds the optical breakdown.

17. A method as recited in claim 11, further comprising the step of selecting the focal spots for each cavity layer so that each cavity layer is substantially flat, substantially circular, and substantially perpendicular to the optical axis.

18. A method as recited in claim 11, further comprising the step of selecting the focal spots for each cavity layer so that each cavity layer has a substantially curved cross-section.

19. A method for modifying the curvature of a cornea of an eye, the eye including a stroma, an epithelium and an optical axis, the method comprising the steps of:

focusing a pulsed laser beam through the epithelium to a substantially spherical, first focal spot in the stroma, the first focal spot having a first central point and a first spot diameter;

pulsing the laser beam at the first focal spot to photodisrupt the stroma and form at the first focal spot a substantially spherical, first cavitation bubble having a first bubble radius;

focusing the laser beam to a substantially spherical, second focal spot in the stroma, the second focal spot having a second central point and a second spot diameter, the second focal spot being substantially adjacent to the first focal spot, the second focal spot having the second spot diameter being substantially equal to the first spot diameter;

pulsing the laser beam at the second focal spot to photodisrupt the stroma and form a substantially spherical, second cavitation bubble having a second bubble radius which is substantially equal to the first bubble radius;

repeating the focusing step and the pulsing step at a plurality of additional focal spots to photodisrupt additional stroma to create a first cavity layer within the stroma, the first cavity layer having a thickness which is substantially equal to the first spot diameter, the first cavity layer having a selected first cavity outer diameter, the first cavity layer being substantially symmetric to the optical axis of the eye;

repeating the focusing step and the pulsing step to create at least one additional cavity layer within the stroma, each additional cavity layer being immediately anterior to a previously formed cavity layer, each additional cavity layer having a selected cavity outer diameter smaller than the previously formed cavity layer, each additional cavity layer being substantially symmetric to the optical axis of the eye; and wherein a spot distance between the first central point and the second central point is equal to between approximately one to two times the first bubble radius.

20. A method as recited in claim 19, further comprising the step of selecting the focal spots for each cavity layer in a spiral pattern which is substantially centro-symmetric relative to the optical axis of the eye.

21. A method as recited in claim 19, wherein the step of focusing the laser beam includes focusing so that the spot distance is equal to between approximately 1.5 times to 1.9 times the bubble radius.

22. A method as recited in claim 19, further comprising the step of selecting the focal spots for each cavity layer so that each cavity layer is substantially flat, substantially circular, and substantially perpendicular to the optical axis.

23. A method as recited in claim 19, further comprising the step of selecting the focal spots for each cavity layer so that each cavity layer has a substantially curved cross-section.

\* \* \* \* \*

UNITED STATES PATENT AND TRADEMARK OFFICE
CERTIFICATE OF CORRECTION

PATENT NO. : 5,993,438
DATED : November 30, 1999
INVENTOR(S) : Juhasz et al.

It is certified that error appears in the above-identified patent and that said Letters Patent is hereby corrected as shown below:

Column 4, Line 50
Following the word "wavelength"
DELETE
[X]
INSERT
--($\lambda$)--

Column 5, Line 53
Following the word "Micrometers"
DELETE
[(1 00 µm)
INSERT
--(100 µm)--

Column 8, Line 10
Following the word "microns"
DELETE
[10 82 m)]
INSERT
--(10µm)--

UNITED STATES PATENT AND TRADEMARK OFFICE
CERTIFICATE OF CORRECTION

PATENT NO. : 5,993,438
DATED : November 30, 1999
INVENTOR(S) : Juhasz et al.

It is certified that error appears in the above-identified patent and that said Letters Patent is hereby corrected as shown below:

Column 9, Line 1
Following the word "In"
DELETE
[Other]
INSERT
--another--

Signed and Sealed this

Eleventh Day of July, 2000

Attest:

Q. TODD DICKINSON

*Attesting Officer*  *Director of Patents and Trademarks*